(12) United States Patent
Issadore et al.

(10) Patent No.: US 11,630,052 B2
(45) Date of Patent: *Apr. 18, 2023

(54) ULTRA-HIGH THROUGHPUT DETECTION OF FLUORESCENT DROPLETS USING TIME DOMAIN ENCODED OPTOFLUIDICS

(71) Applicant: The Trustees of the University of Pennsylvania, Philadelphia, PA (US)

(72) Inventors: David A Issadore, Philadelphia, PA (US); Venkata Yelleswarapu, Philadelphia, PA (US)

(73) Assignee: The Trustees of the University of Pennsylvania, Philadelphia, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/017,966

(22) Filed: Sep. 11, 2020

(65) Prior Publication Data
US 2021/0239593 A1 Aug. 5, 2021

Related U.S. Application Data

(63) Continuation of application No. 16/344,385, filed as application No. PCT/US2017/057869 on Oct. 23, 2017, now Pat. No. 10,809,176.

(Continued)

(51) Int. Cl.
*G01N 15/14* (2006.01)
*B01L 3/00* (2006.01)
(Continued)

(52) U.S. Cl.
CPC .... *G01N 15/1434* (2013.01); *B01L 3/502715* (2013.01); *B01L 3/502784* (2013.01);
(Continued)

(58) Field of Classification Search
CPC .......... G01N 15/1434; G01N 15/1425; G01N 15/1429; G01N 15/1459; G01N 15/1463;
(Continued)

(56) References Cited

U.S. PATENT DOCUMENTS 9,817,016 B1* 11/2017 Tracy ................... G01F 1/7086
2004/0105499 A1 6/2004 Kawa et al.
(Continued)

FOREIGN PATENT DOCUMENTS

WO 2015/157369 A1 10/2015
WO 2016/025809 A1 2/2016

OTHER PUBLICATIONS

Kim, M. et al., "Optofluidic ultra-high-throughput detection of fluorescent drops," Lab Chip 15, 1417-1423 (2015).
(Continued)

*Primary Examiner* — Kiet T Nguyen
(74) *Attorney, Agent, or Firm* — BakerHostetler

(57) ABSTRACT

A high-throughput optofluidic device for detecting fluorescent droplets is disclosed. The device uses time-domain encoded optofluidics to detect a high rate of droplets passing through parallel microfluidic channels. A light source modulated with a minimally correlating maximum length sequences is used to illuminate the droplets as they pass through the microfluidic device. By correlating the resulting signal with the expected pattern, each pattern formed by passing droplets can be resolved to identify individual droplets.

11 Claims, 18 Drawing Sheets

Related U.S. Application Data

(60) Provisional application No. 62/411,919, filed on Oct. 24, 2016.

(51) Int. Cl.

| | | |
|---|---|---|
| *G01N 21/64* | (2006.01) | |
| *C12M 1/00* | (2006.01) | |
| *G01N 21/00* | (2006.01) | |
| *G06V 10/141* | (2022.01) | |
| *G06V 20/69* | (2022.01) | |
| *G01N 15/10* | (2006.01) | |
| *G01N 15/00* | (2006.01) | |
| *G01N 21/17* | (2006.01) | |

(52) U.S. Cl.
CPC ............... *C12M 1/00* (2013.01); *G01N 15/14* (2013.01); *G01N 15/1425* (2013.01); *G01N 15/1429* (2013.01); *G01N 15/1436* (2013.01); *G01N 15/1459* (2013.01); *G01N 15/1463* (2013.01); *G01N 21/00* (2013.01); *G01N 21/645* (2013.01); *G06V 10/141* (2022.01); *G06V 20/69* (2022.01); *B01L 2200/0673* (2013.01); *G01N 2015/0053* (2013.01); *G01N 2015/1006* (2013.01); *G01N 2015/144* (2013.01); *G01N 2021/177* (2013.01); *G01N 2021/1757* (2013.01); *G01N 2021/1765* (2013.01); *G01N 2201/0221* (2013.01); *G01N 2201/0625* (2013.01); *G01N 2201/0696* (2013.01)

(58) Field of Classification Search
CPC .... G01N 15/14; G01N 15/1436; G01N 21/00; G01N 21/645; G01N 2015/0053; G01N 2015/1006; G01N 2015/144; G01N 2021/1757; G01N 2021/1765; G01N 2021/177; G01N 2201/0221; G01N 2201/0625; G01N 2201/0696; G06K 9/00127; G06K 9/2027; B01L 3/502715; B01L 3/502784; B01L 2200/0673; C12M 1/00; G06V 10/141; G06V 20/69
USPC ........................................................ 250/251
See application file for complete search history.

(56) References Cited

U.S. PATENT DOCUMENTS

| | | |
|---|---|---|
| 2004/0146917 A1 | 7/2004 | Cork et al. |
| 2007/0159627 A1 | 7/2007 | Johnson |
| 2010/0041086 A1 | 2/2010 | Pamula et al. |
| 2011/0000560 A1 | 1/2011 | Miller et al. |
| 2011/0309276 A1 | 12/2011 | Worsman et al. |
| 2012/0135874 A1 | 5/2012 | Wang et al. |
| 2012/0157160 A1 | 6/2012 | Ozcan et al. |
| 2014/0309795 A1 | 10/2014 | Norton et al. |
| 2014/0354795 A1 | 12/2014 | Tracy et al. |
| 2017/0307502 A1* | 10/2017 | Mason .................. B01L 3/0241 |
| 2018/0306709 A1* | 10/2018 | Zaccari .............. G01N 21/3103 |

OTHER PUBLICATIONS

Muluneh et al., "Miniaturized, multiplexed readout of droplet-based microfluidic assays using time-domain modulations", Lab Chip, Dec. 21, 2014, 14(24), 4638-4646.

Siva Gorthi Sai et al: "Fluorescence imaging of flowing cells using a temporally coded excitation", Optics Express, vol. 21, No. 4, Dec. 31, 2013 (Dec. 31, 2013), pp. 5164-5170, XP055692834.

* cited by examiner

Algorithm Work Flow

MLS Lock-in Detection

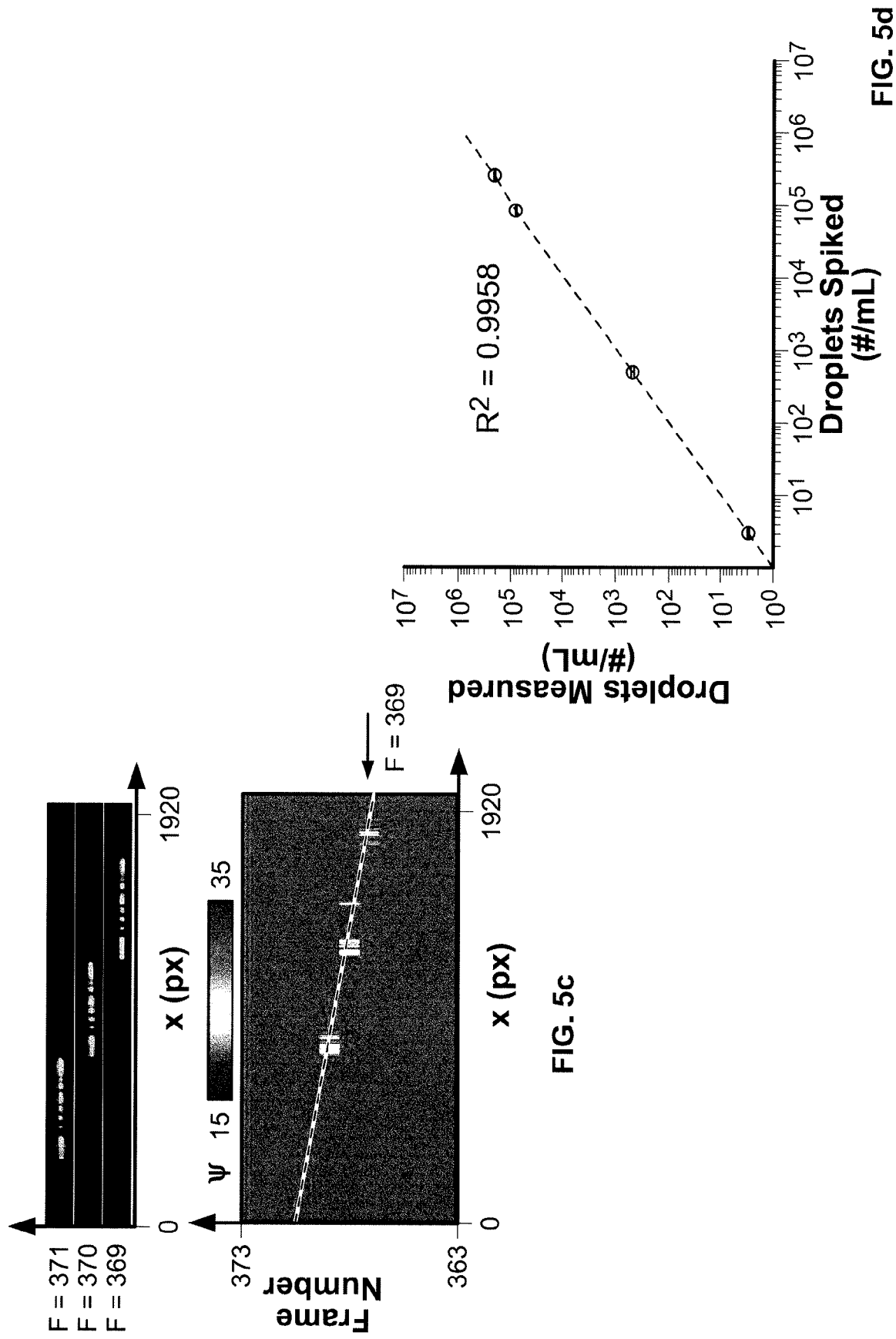

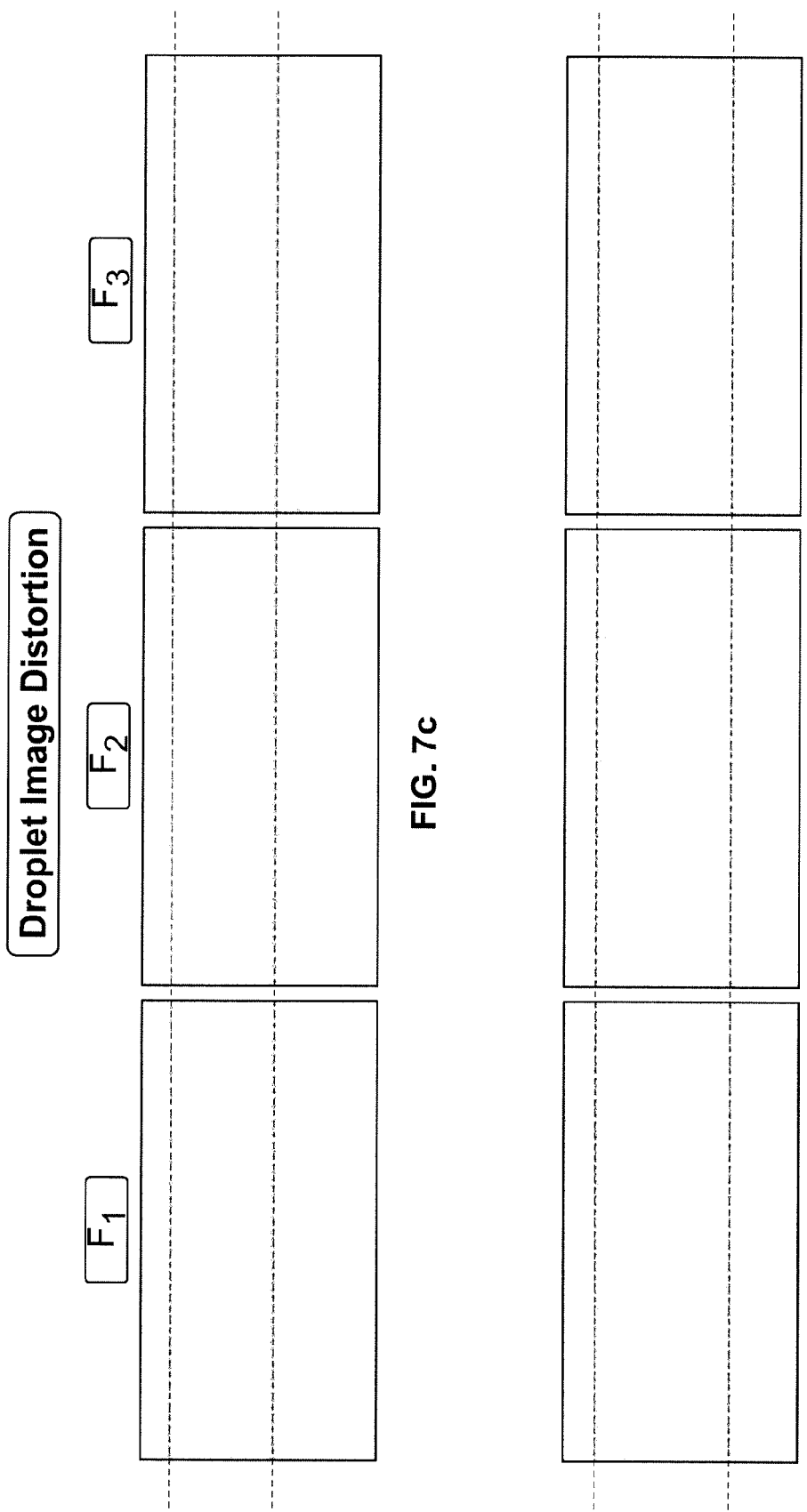

US 11,630,052 B2

ULTRA-HIGH THROUGHPUT DETECTION OF FLUORESCENT DROPLETS USING TIME DOMAIN ENCODED OPTOFLUIDICS

CROSS-REFERENCE TO RELATED APPLICATIONS

This application is a continuation of U.S. application Ser. No. 16/344,385, filed Apr. 24, 2019 (now allowed), which is the National Stage Application of International Patent Application No. PCT/US2017/057869 filed Oct. 23, 2017, which claims the benefit of U.S. Provisional Application No. 62/411,919, filed Oct. 24, 2016, the contents of which foregoing applications are incorporated herein by reference in their entireties for all purposes.

FIELD OF THE INVENTION

The present invention relates to the detection of fluorescent droplets using time domain encoded optofluidics.

INTRODUCTION

Droplet-based assays, in which microscale emulsions are used as isolated compartments to run many independent chemical reactions, have generated enormous enthusiasm in recent years as a platform for the ultrasensitive detection of small molecules, proteins, and nucleic acids. The sensitivity of droplet-based assays arises from the $10^6\times$ reduction of the microliter (µL) volumes of fluid used in conventional laboratory assays to picoliter (pL) volumes. However, the enormous increase in sensitivity that arises from massively parallelized, ultra-small volume assays comes at the expense of requiring cumbersome instrumentation (pumps, optics, multiple microfluidic chips) and time-consuming processing (T>1 hour for current commercial systems) to generate, process, and measure millions of droplets. This processing time is limited by the inherently low throughput ($10^3$ droplets/sec) in which microscale droplets can be generated and fluorescently detected using conventional techniques.

One promising direction to scale-up droplet production and detection has been the development of platforms that make it possible to operate many microfluidic droplet generators and detectors in parallel. To this end, imaging platforms have been designed to measure many droplets simultaneously. Alternatively, in-flow detection systems, can measure a far greater number of droplets than possible with the static techniques, and have the advantage that droplets can be sorted downstream of the detector.

One microfluidic technique that has been developed in an attempt to simplify detection without expensive lenses, cameras, and lasers uses spatial modulation to monitor parallel droplets or cells using a single photodetector. See, e.g., Muluneh et al., "Miniaturized, multiplexed readout of droplet-based microfluidic assays using time-domain modulations," Lab Chip 14, 4638-46 (2014).

In another approach, a hybrid CMOS/microfluidic chip was reported that can detect droplets in-flow, in many parallel channels, achieving very high throughput (254,000 droplets/sec). See Kim, M. et al., "Optofluidic ultra-high-throughput detection of fluorescent drops," Lab Chip 15, 1417-1423 (2015). The method disclosed by Kim et al. requires a specialized microfluidic device in which the microfluidic channels are fabricated directly on a CMOS chip and uses a high frame rate (2125 fps) to capture a four pixel-wide image that approximates the width of the individual droplets.

However, these developments have been limited by their need for specialized, expensive high frame rate cameras, are limited to measuring the number of droplets that can be packed into a single image (<1 million), limiting dynamic range, or require disposable microfluidic chips that incorporate expensive (>$10/chip) CMOS chips.

SUMMARY OF THE INVENTION

Aspects of the present invention relate to devices and methods for detecting droplets using optofluidics.

A first aspect of the present invention relates to a method for detecting fluorescent droplets comprising:
  generating a plurality of droplets and flowing the droplets through at least one channel of a microfluidic device;
  illuminating the droplets with a time-domain modulated sequence of flashes from a light source, wherein the time-domain modulated sequence has a duration, d; and
  capturing at least one image of the at least one channel, wherein the image has an exposure time, t, greater than or equal to the duration, d, of the time-domain modulated sequence.

A second aspect of the present invention relates to a device for detecting fluorescent droplets comprising:
  a droplet generator in a microfluidic channel;
  a light source for illuminating droplets in the microfluidic channel;
  a controller for flashing the light source in a time-domain modulated sequence; and
  a photo sensor for capturing an image of the microfluidic channel

BRIEF DESCRIPTION OF THE DRAWINGS

FIG. 5*c* shows three frames as the droplet travels through and the corresponding correlation heatmap according to an embodiment of the present invention.

FIG. 5*d* shows the dynamic range that can be covered by an embodiment of the present invention.

FIGS. 7*c* and 7D show the initial distortion and subsequent correction, respectively, according to an embodiment of the invention.

DETAILED DESCRIPTION OF THE INVENTION

Aspects of the invention are directed to devices and processes for detecting fluorescent droplets in microfluidic devices.

Figure 1A:
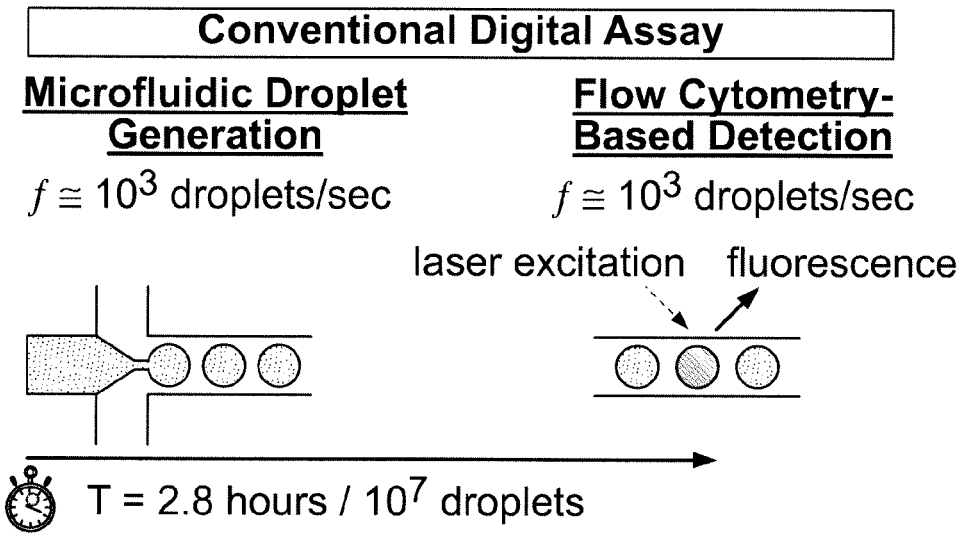
FIG. 1a shows a conventional digital assay.
Figure 1B:
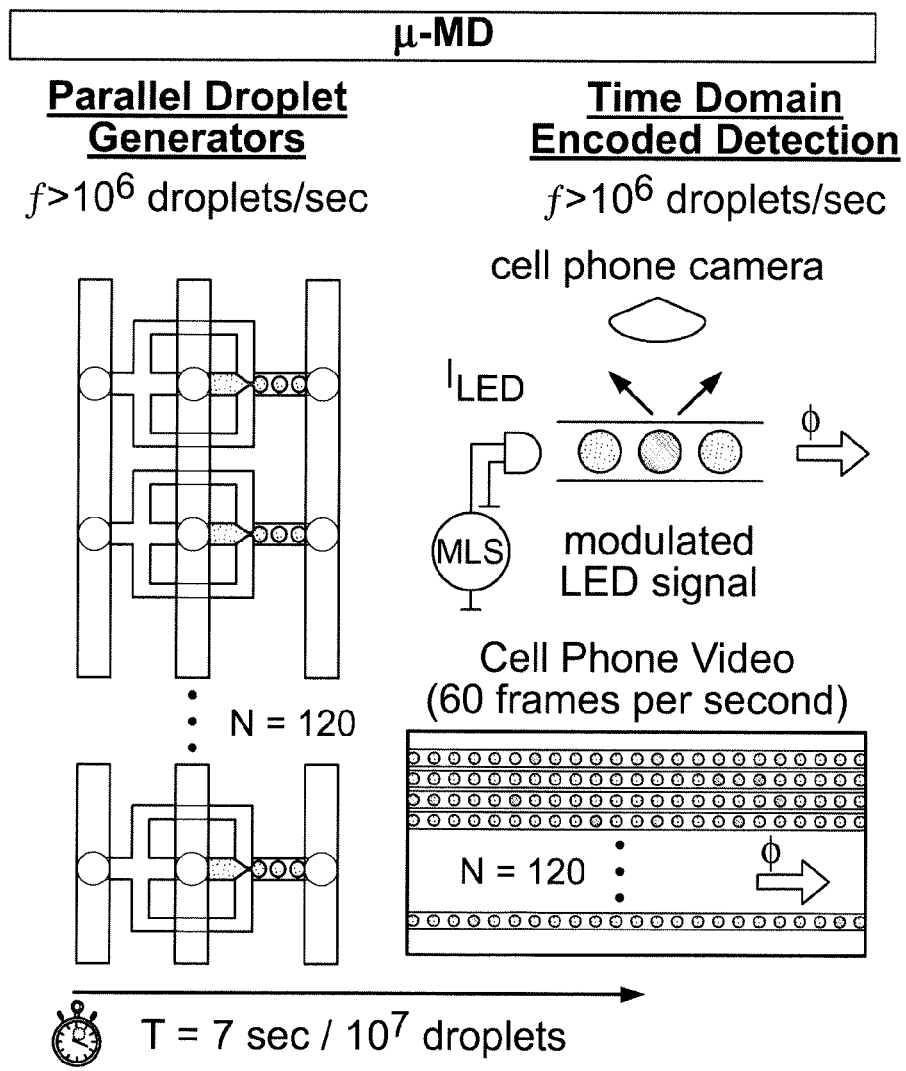
FIG. 1b shows a schematic representation of a parallel droplet generator and fluorescent detection apparatus according to an embodiment of the invention.
Figure 1C:
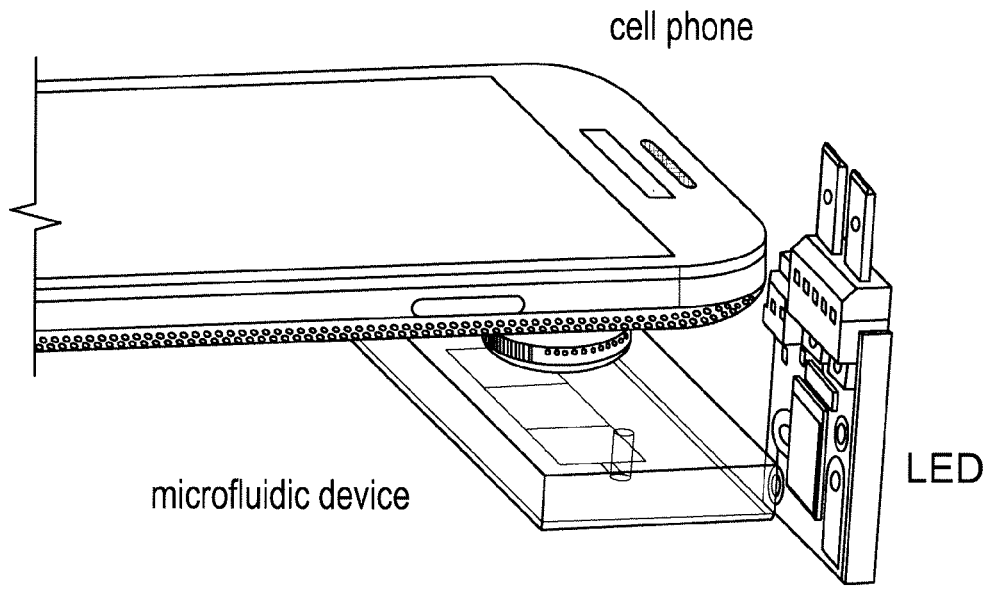
FIG. 1c shows a schematic representation of a cell phone camera being used as the detector according to an embodiment of the invention.
Figure 1D:
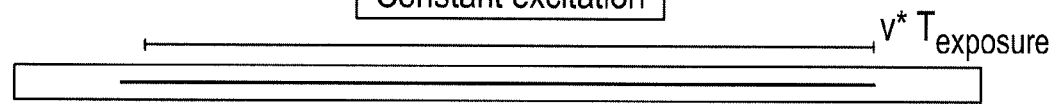
FIG. 1d shows an image of a passing droplet with constant LED illumination.

The inventors have recognized that it would be useful to use inexpensive cameras to detect fluorescent droplets in microfluidic devices. Typically, inexpensive cameras are unable to resolve droplets in microfluidic devices because the speeds at which droplets travel through microfluidic channels results in blurred images. Constant illumination of the microfluidic channel results in images in which a fluorescent droplet shows up as a blurred streak (FIG. 1*d*). The blurred streak makes it difficult or even impossible to resolve individual droplets, or to even determine whether multiple droplets are present. Although the detection of droplets is discussed throughout the present disclosure and in the examples, it is understood that the processes and techniques described herein are also applicable to other discrete objects that may be detected through imaging, such as cells and beads.

Figure 1E:
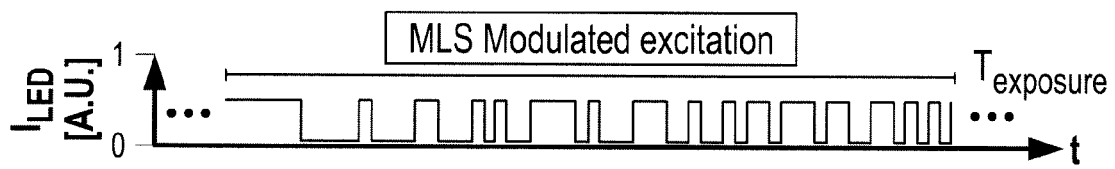
FIG. 1e shows a maximum length sequence (MLS) modulated excitation scheme according to an embodiment of the invention.
Figure 1F:
FIG. 1f shows an image of a passing droplet illuminated by the MLS modulated excitation scheme of FIG. 1e.
Figure 1G:
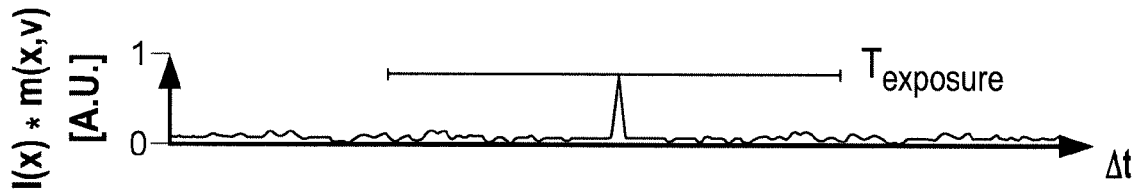
FIG. 1g shows the resolution of a sharp peak after correlating the signal with the expected pattern resulting from the MLS modulation scheme shown in FIG. 1e.

The inventors have recognized that individual droplets can be identified using time-domain modulated sequences of light flashes. Rather than using constant illumination, the embodiments of the present invention use time-domain modulated sequences to illuminate the microfluidic channels with a sequence of flashes (FIG. 1*e*). The use of a time-domain modulated sequence of flashes results in an image with a sequence of blurred lines corresponding to the flashes of light (FIG. 1*f*). By correlating the captured image with the expected pattern, each pattern can be resolved into a sharp peak corresponding to an individual droplet (FIG. 1*g*).

According to at least one embodiment of the present disclosure, the microfluidic device may comprise any microfluidic device having a channel that can be imaged. The microfluidic device or chip can comprise a simple structure having one or more channels formed therein. The microfluidic device may comprise a droplet generator and at least one channel through which the droplets may flow.

According to at least one embodiment, the microfluidic device comprises a plurality of channels, each of which comprises a droplet generator. The throughput of the present device is linearly scalable with the number of channels. The channels may be dimensioned to accurately control the passage of the droplets. For example, the channels may have a width slightly larger than the diameter of the droplets to avoid clustering of the droplets. In some situations, however, it may be desirable to use channels significantly larger than the diameter of the droplet.

Inexpensive cameras can be used to capture images according to embodiments of the present invention. For example, such inexpensive cameras include the cameras on cellular phones or simple point-and-shoot cameras. Such cameras typically use small complementary metal-oxide-semiconductor (CMOS) photo sensor arrays. For cellular cameras, these CMOS photo sensors are typically on the order of a few millimeters per side (1/3.2" diagonal). Larger photo sensors and different types of photo sensors (e.g., CCD sensors) may be used to improve the throughput and/or resolution. For example, point-and-shoot cameras may have a sensor up to 1" diagonal, a digital SLR camera may have a sensor up to 35 mm diagonal, and a medium format camera may have a photo sensor two to six times larger than a 35 mm "full frame" DSLR. The improved performance of larger sensors comes at a tradeoff of portability and price.

In at least one embodiment, the photo sensor is capable of recording images or video at speeds of 30 frames per second (fps) or more, such as, for example, 60 fps, 120 fps, 240 fps, or more. Increasing the frame rate of the photo sensor generally increases the resolution and potential throughput of the device.

The device may further comprise filters to enhance or improve the signal from the fluorescent droplets.

According to at least one embodiment, the light source is one which may be precisely controlled at high speeds. For example, the light source may comprise a light emitting diode (LED). In at least one embodiment, the light source may comprise more than one light source, such as, for example, two or more LEDs that emit different wavelengths. Due to the physical separation of the channels, it is possible to multiplex the detection mechanism to detect a wide array of biomarkers simultaneously and track the abundance of each type using the channel separation.

Illumination of the light source can be controlled by a controller, such as a microcontroller like the Arduino, an open-source electronic prototyping platform which allows users to control electronic objects.

The light source is illuminated using a sequence of flashes. Using time-domain modulated sequences, the inventors have recognized that it is possible to resolve individual droplets from images of droplets passing through microfluidic channels, even when the droplets are moving at high speeds.

In at least one embodiment, the light source is flashed or blinked using maximum length sequences (MLSs). A maximum length sequence is a pseudorandom binary sequence (e.g., signals the light source to turn on or off) typically used in digital telecommunications.

According to at least one embodiment, the MLS is a minimally corresponding MLS. The minimally corresponding MLS has a sequence that differs throughout the sequence, i.e., the duration of the signals for "on" and "off" changes throughout the sequence. In at least one embodiment the MLS has a beginning sequence that differs from the end sequence. As used herein, the terms "beginning sequence" and "end sequence" refer to the portions of the MLS at the start of the sequence and at the end of the sequence, such as, for example, the first half of the sequence and the second half of the sequence.

In at least one further embodiment, the MLS may also comprise a middle sequence that differs from the beginning sequence and the end sequence. As used herein, the term "middle sequence" refers to the portion of the MLS between the beginning sequence and the end sequence. For example, the middle sequence can be the middle third of the sequence and the beginning and end sequences can be the outer thirds of the sequence.

As used herein, the term "differs" with respect to the time-domain modulated sequences refers to the pattern and/or duration of portions of the sequence, e.g., the beginning sequence and the end sequence.

For example, the beginning and end sequences can differ in the pattern of the signal, e.g., the duration of the on/off signals and the spaces between "on" signals. Similarly, the portions of the sequences can differ based on the average duration of the signals.

In at least one embodiment, the portions of the sequence can have similar average duration of the signals but still differ based on the pattern of duration. For example, the beginning portion may comprise a sequence of very short and very long "on" signals that have the same average duration as an end sequence that comprises a series of medium duration "on" signals.

In other embodiments, the portions of the sequence can differ in both duration and pattern of the signals.

According to at least one embodiment, the portions of the signals differs by at least 10%, such as at least 20%, at least 30%, at least 40%, at least 50%, at least 60%, at least 70%, at least 80%, at least 90%, or more. The percentage that one sequence differs from the other may be measured by the amount of overlap of the sequence or by the average duration of the signals in the sequences.

According to at least one embodiment, the length of the time-domain modulated sequence is less than the length of the exposure time of the acquired image. For example, if the image is a frame from a video shot at 30 fps, the length of the time-domain modulated sequence can be $\frac{1}{30}$ sec or less. Similarly, if the image is a frame from a video shot at 60 fps, the length of the time-domain modulated sequence can be $\frac{1}{60}$ sec or less. Although it is possible to use a sequence that is longer than the exposure time of the image, the resulting analysis may be more complex.

According to at least one embodiment, the image can be analyzed by correlating the acquired image with the expected image based on the time-domain modulated sequence of light flashes. Because the sequence is known, the small streaks of light corresponding by fluorescent material in the droplets can be resolved to identify individual droplets.

The device according to embodiments of the present disclosure may be a portable device, e.g., using a portable camera, or a lab device.

Although the invention is illustrated and described herein with reference to specific embodiments, the invention is not intended to be limited to the details shown. Rather, various modifications may be made in the details within the scope and range of equivalents of the claims and without departing from the invention.

EXAMPLES

The exemplary microdroplet Megascale Detector (µMD) in accordance with embodiments of the present disclosure may generate and detect the fluorescence of millions of droplets per second (1000× faster than conventional approaches). By strobing the excitation light with a pseudorandom time-domain modulated sequence, a 100× faster throughput than possible using a continuous light source. The µMD measures droplets at a rate of $10^6$ droplets/sec (ϕ=160 mL/hr) in 120 parallel microfluidic channels, a limit of detection LOD<1 µM rhodamine dye, sufficient for conventional droplet based assays, and a dynamic range of $\frac{1}{10^7}$ to $\frac{1}{30}$ (positive/negative droplets). The exemplary µMD incorporates 120 parallel droplet makers and only one set of oil, aqueous, and output line. By miniaturizing and integrating droplet based diagnostics into a handheld format, the µMD platform can translate the ultra-sensitive droplet based assays now being developed in a self-contained platform for practical use in clinical and industrial settings.

The µMD is a disposable microfluidic chip fabricated using only plastic and requires no active components, enabling extremely low cost implementation (<10¢/chip). In addition, since the chip is only used for droplet flow, there is no need to sterilize the chip or functionalize it with antibodies that need to be handled carefully. The example below demonstrates the use of conventional cell phone cameras to demonstrate the ability of droplet microfluidics to be used in point of care applications due to the ubiquitous availability of smart phones, with their sensitive cameras and connection to cloud computing.

The μMD uses only a cell phone camera with commercial lenses that are <$4, and an LED that is modulated with an Arduino. The reusable component of the μMD consists of a microfluidic chip made of only PDMS and glass, where each chip simply slides into a 3D printed casing that automatically aligns the chip and keeps the process extremely inexpensive (FIG. 1c). Unlike high frame rate recording devices, cell phone cameras are typically hindered by the low frame rate. The low frame rate causes droplets to show up as streaks during recording (FIG. 1d), and is a limiting factor for the dynamic range where overlapping streaks cannot be resolved as individual droplets. To solve this, the droplets were patterned by blinking the LED in minimally correlating Maximum Length Sequences (MLS) (FIG. 1e), allowing each pattern in space to be resolved into a sharp peak after correlating the signal with the expected pattern (FIGS. 1f and 1g). The μMD enabled droplet microfluidic detection with cell phone based cameras at extremely high throughput ($\phi$=100 mL/hr), sensitivity comparable to traditional techniques (1 μM), and a dynamic range that reflects the typical ratios needed for digital assays (1:10$^7$ to 1:300).

Methods

Device Fabrication and Optics Design

The chip was fabricated using traditional soft lithography to make the fluidic channels that were then plasma bonded to a glass slide. The PDMS layer was fabricated using single-layer SU-8 lithography (SU-8 2050, Microchem) with 50 μm thick features to accommodate for the 40 μm droplets.

Figure 7A:
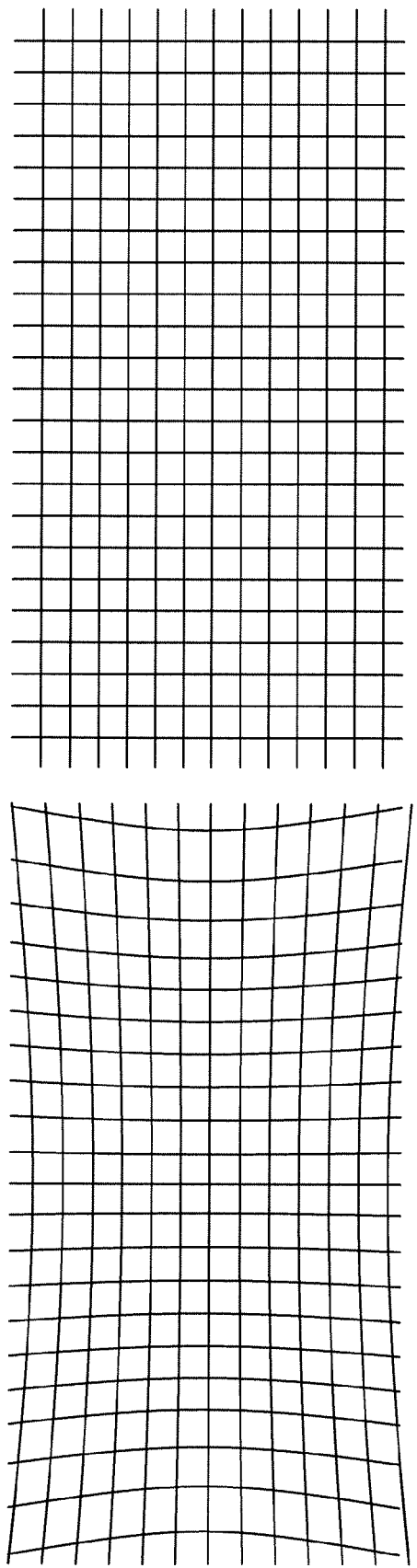
FIGS. 7*a* and 7*b* show the pincushion distortion caused by the macro lens used in accordance with an embodiment of the invention and the correction of the distortion using Matlab.
Figure 7B:
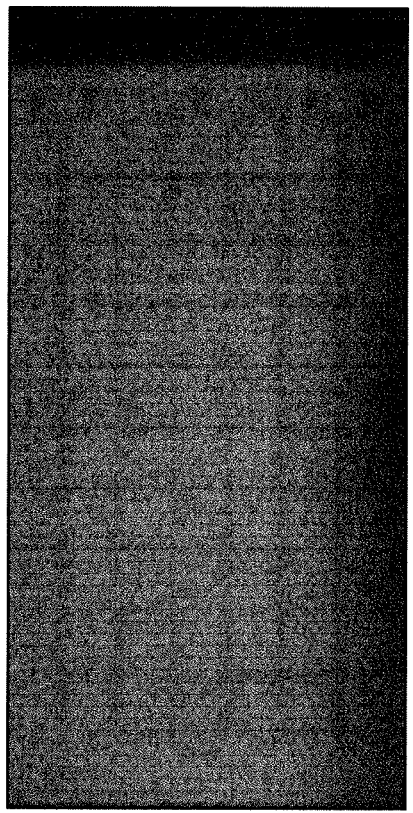
Figure 7B:
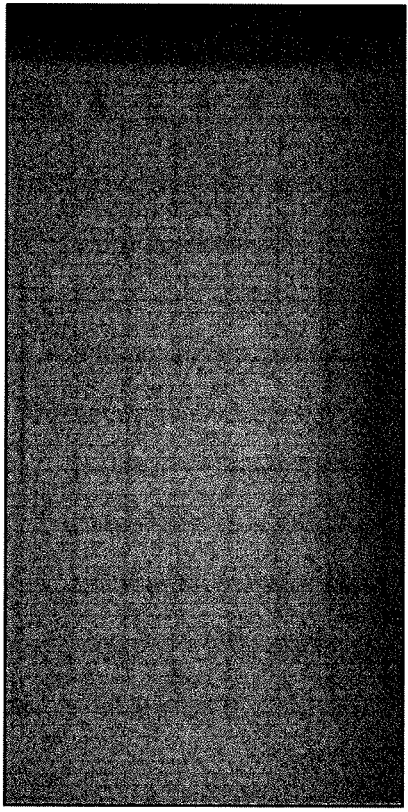

In order to keep the optics as inexpensive as possible, a commercial clip-on macro lens was used in series with a longpass filter fitted directly into an acrylic casing to keep a small-footprint product. An ultra-bright LED ($\lambda$ex=530 nm) (Luminus, CBT-90-G-C11-JK201) provided the excitation light, which was connected to an LED driver (Luminus Development Kit, DK-114N-3). The development kit allowed LED modulation up to 40 kHz using standard TTL response to turn the LED on or off based on a user generated signal from an Arduino Mega2560. The housing for the microfluidic chip was designed such that the PDMS chip had maximum anti-resonant coupling to ensure the excitation light spread evenly throughout the entire chip. A 605 nm long pass filter (Edmund Optics, #52-528) was placed between the chip and lens to diminish (95% reflectance) the effect of scattered light at the excitation wavelength. Finally, an inexpensive (<$4), 15× commercially available macro lens (Carson HookUpz, ML-515) was placed directly in front of the cell phone camera such that the spacing between the microfluidic channels and the lens was 0.5 inches. Due to spherical aberration from this lens, software was used to undistort images rather than resort to expensive optical solutions (FIG. 7). A checkerboard pattern was used to calibrate the distortion, and then MATLAB's Computer Vision System Toolbox was used to undistort the droplet images to transform the pincushion aberration into a flat 2d image where the channels be segmented properly.

Cell Phone Parameters

Unlike traditional scientific CMOS camera where the user is in control of most image acquisition parameters, a cell phone camera has only a handful of features that need to be optimized prior to recording. Using a Samsung Galaxy S7 Edge's Camera "Pro" Mode, the following settings were used to record: (i) the focus was manually fixed so the chip could slide in to an acrylic casing without having to align the chip, (ii) the ISO was set to 3200 and Exposure to +2 to maximize light input unless specified otherwise, (iii) aperture was set to 1/30, (iv) metering mode was set to Matrix, and (v) the color correction was set to Auto. All videos were recorded 1920×1080p size at 60 fps or 30 fps using the OpenCamera App, since this setting captured all 120 channels properly without extremely large file sizes, with a field of view of ~12 mm by 7 mm. While higher resolution videos could be captured, this would have created file sizes that would take much longer to analyze without significantly increasing the field of view. The video was then transferred to a personal computer to analyze for droplet detection. All analysis was done in MATLAB on a personal computer, but cloud computing could be used for a complete portable implementation.

LED Modulation and Streak Patterning Design

The LED modulation sequence was selected such that: (i) patterns were minimally correlated with themselves and (ii) the lengths of the pattern were long enough to create sharp peaks within the number of pixels set by the length of the imaging region (1920 px). To generate these patterns, a mathematical framework for applications in radar and telecommunications developed to generate maximally uncorrelated, pseudorandom sequences was used.

The length of the mask patterns for the device that we designed was 63 bits. The sequence was made as long as possible to minimize each channel's autocorrelation. The length was constrained by the camera's ability resolve bits and the length of the imaging region. The Samsung Galaxy S7 used had a detection region of 7×12 mm$^2$. The size of each "bit" in the sequence was set to ~10 pixels on the CMOS detection region while recording at 1080p (1920× 1080 pixels). Based on this selection, a full droplet streak with the chosen velocity would correspond to ~⅓ of the frame. The generated MLS from MATLAB was then exported and loaded into the Arduino Mega, which controlled when the LED was on/off. For example, if a 63-bit MLS was desired for a passing droplet at 60 fps recording, the MLS was repeated every ~17 ms, with each bit consisting of $\Delta t$=~0.25 ms. Thus, the number of time spent on each bit can be given by the equation:

$$t_{bit} = \frac{1s}{\text{frame rate} * N_{bits}}$$

It was confirmed that the Arduino was able to modulate the LED at this rate by measuring the output from the Arduino with a NI DAQ board with sampling rate of 1 GHz (NI SCB-68A/USB X Series). It was also verified that the LED response matched the Arduino MLS output pattern using a Si Photodetector (PDA100A, Thorlabs) to ensure that the LED and Arduino were able to properly output the desired temporal MLS.

Results

Due to the low frame rate of the cell phone camera (<240 fps), a passing fluorescent droplet looks like a streak since multiple pixels are exposed to the passing light during the time a droplet passes across the detection region (FIG. 1e). However, when multiple fluorescent droplets pass together, it becomes impossible to differentiate the droplets from each other. Without the ability to resolve multiple droplets passing in close proximity, the dynamic range for the system is severely limited, requiring samples to be diluted to large volumes and increase interrogation time or use samples with a confined dynamic range. Thus, time encoding serves two purposes: (i) resolve overlapping droplets as sharp peaks through correlation that can be resolved into individual droplets, and (ii) recover signals below the noise floor.

Signal Extraction

Figure 2A:
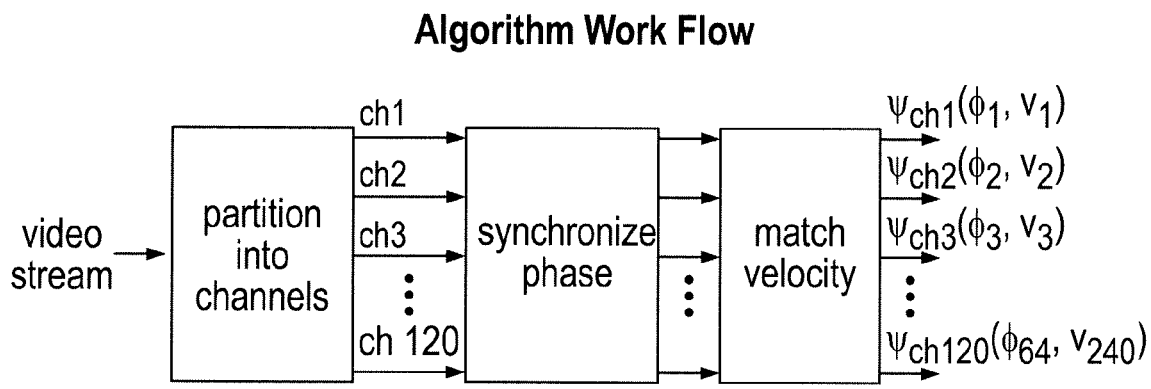
FIG. 2a shows a schematic representation of the workflow for analyzing an acquired fluorescence image according to an embodiment of the invention.
Figure 2B:
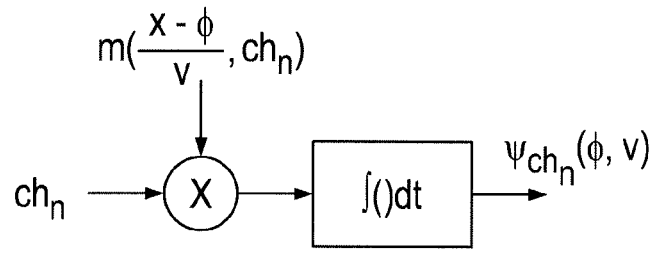
FIG. 2b shows a schematic representation of the workflow for acquiring the correlation vector according to an embodiment of the invention.

Briefly, the algorithm workflow of the system was as follows: (i) a video stream recorded of the droplets was reviewed frame by frame; (ii) each channel was partitioned into channels by the physical location of the pixels of the CMOS camera (FIG. 2c, 2d), (iii) for each given channel, one phase was first picked and several velocities were scanned through for the given phase, and optimal velocity for the given phase was found (iv). The strongest fitting correlation peak was recovered for each channel based on the appropriate velocity and phase of the droplet's pattern after removing any offset from noise with a high pass filter (FIG. 2b).

Figure 2C:
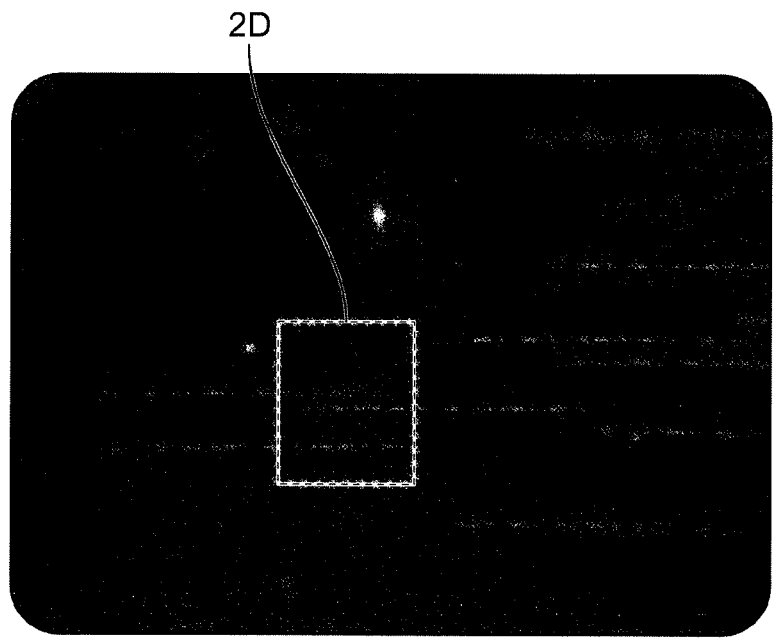
FIG. 2c shows a single frame of an image showing several droplets passing through according to an embodiment of the invention.
Figure 2D:
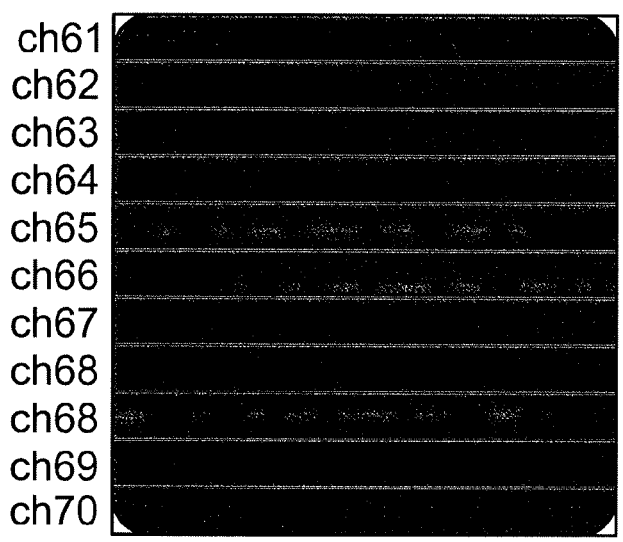
FIG. 2d shows an enlarged portion of the frame shown in FIG. 2c.
Figure 2E:
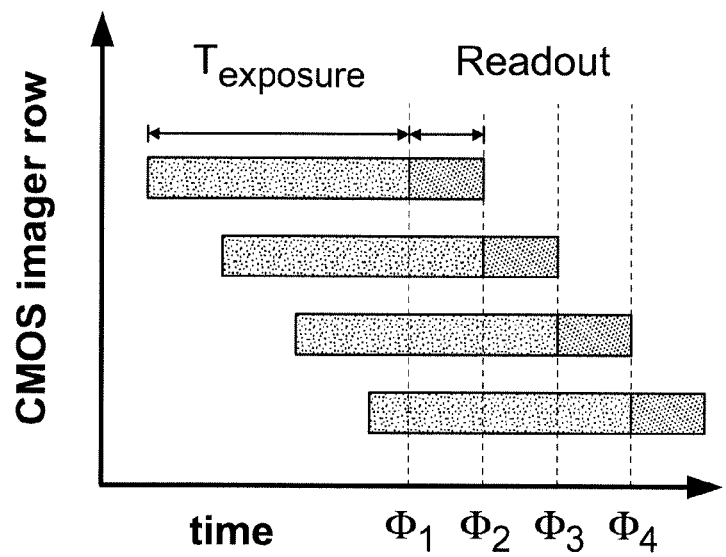
FIG. 2e is a schematic representation of the rolling shutter effect acquired in images according to an embodiment of the invention.
Figure 6A:
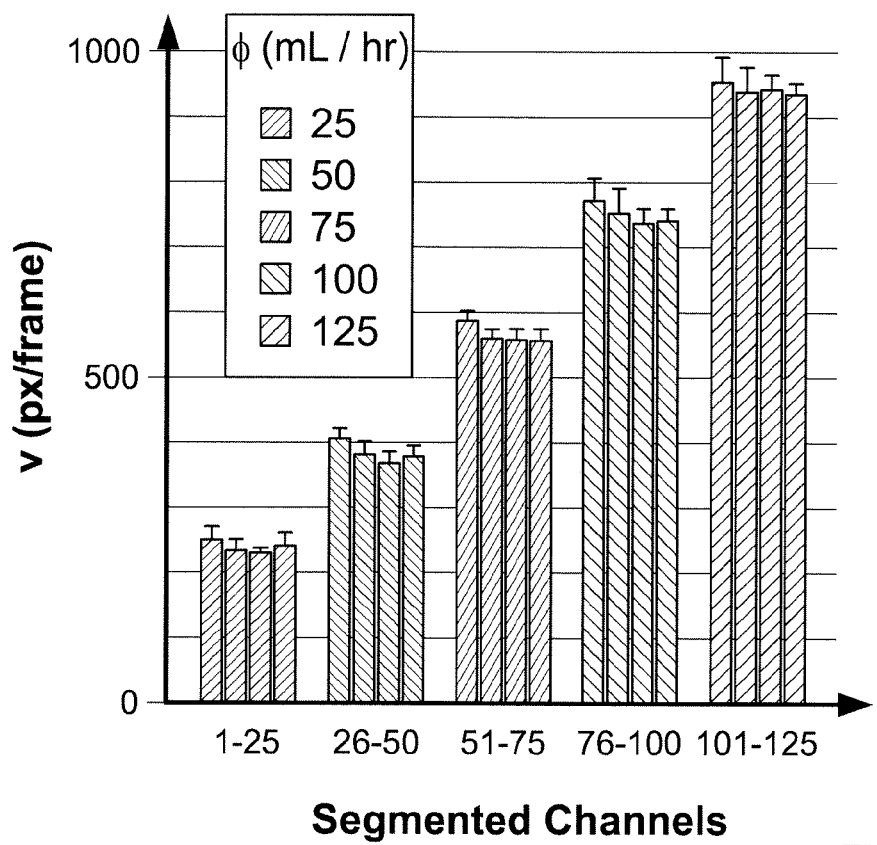
FIG. 6*a* shows a graph demonstrating the variation in flow rate across different channels at a given flow rate with error bars representing the standard deviation according to an embodiment of the present invention.
Figure 6B:
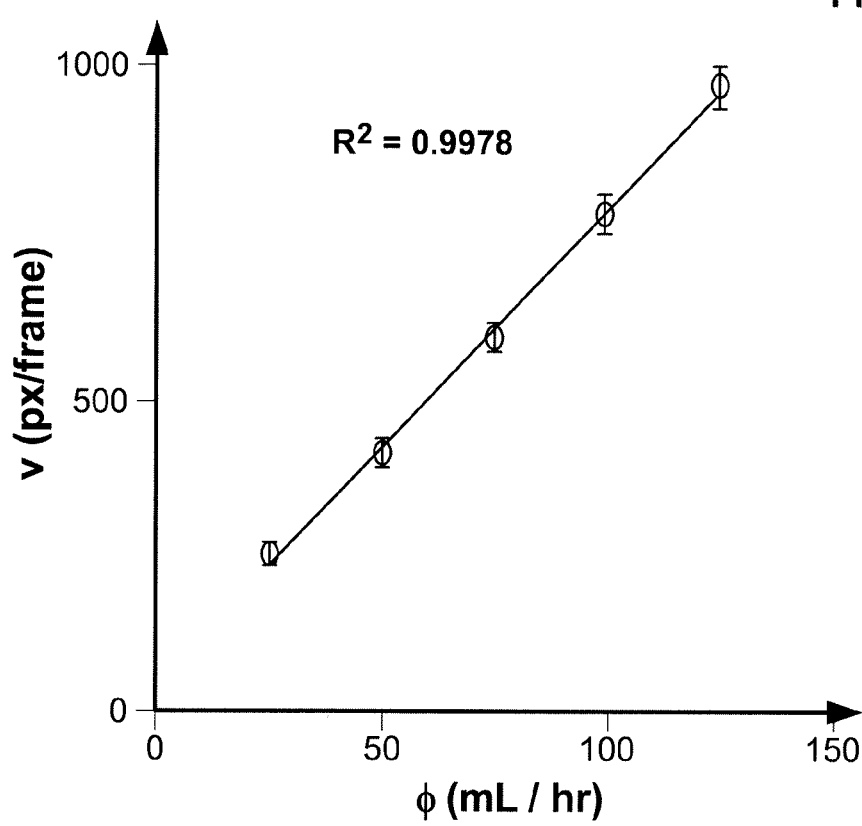
FIG. 6*b* shows a graph of the droplet velocity recorded as a function of the flow rate with error bars showing the standard deviation at each of the given data points according to an embodiment of the present invention.

A single frame is shown with several droplets passing (FIG. 2c). The number of pixels that fit on a camera frame at 1920×1080p gives a width consisting of 1920 pixels for one channel and a length of 1080 px, for a field of view corresponding to 12 mm×7 mm. For 120 channels, each channel was partitioned into 1080 pixels/120~9 pixels/channel and channels were thus defined based on the physical mapping of the image onto the CMOS sensor (FIG. 2d). However, the camera does not take an entire image at once, but instead records the intensities for each row—termed the rolling shutter effect. This lag between the time of exposure and readout caused a delay between the different rows on the CMOS sensor. The blinking LED did not create a single pattern for all the rows in a given frame, but instead caused the pattern to be phase shifted based on this readout offset for each row (FIG. 2e). Thus, the resulting pattern to be identified for each droplet could be phase shifted from the rolling shutter effect and from the setup where the LED and cell phone are not perfectly synced for each frame. Therefore, while droplets at a given flow rate traveled at a narrow range of velocities (CV=4.4% at 100 mL/hr) (FIG. 6), it was necessary to identify the optimal phase and velocity before detecting a droplet.

Figure 2F:
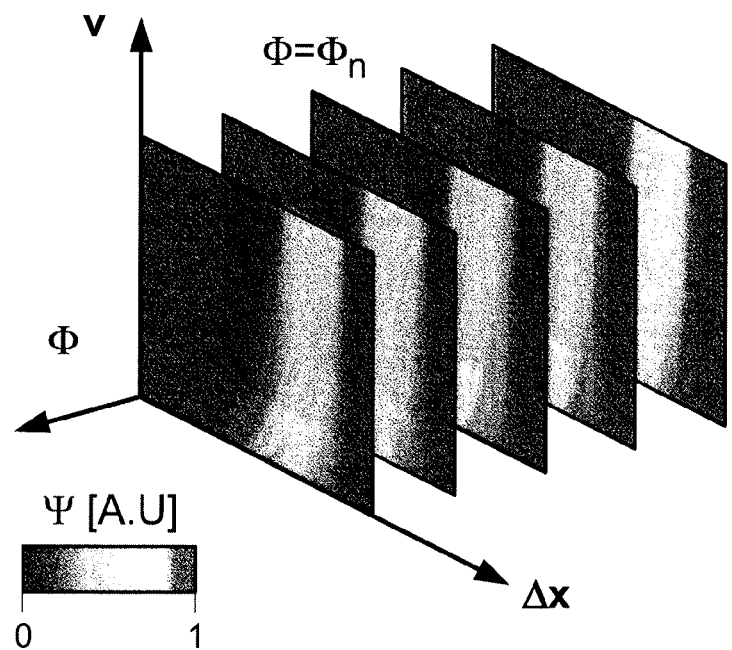
FIG. 2*f* is a schematic representation of a 3D matrix consisting of data that has correlation intensities for phases and velocities to be examined according to an embodiment of the invention.
Figure 2G:
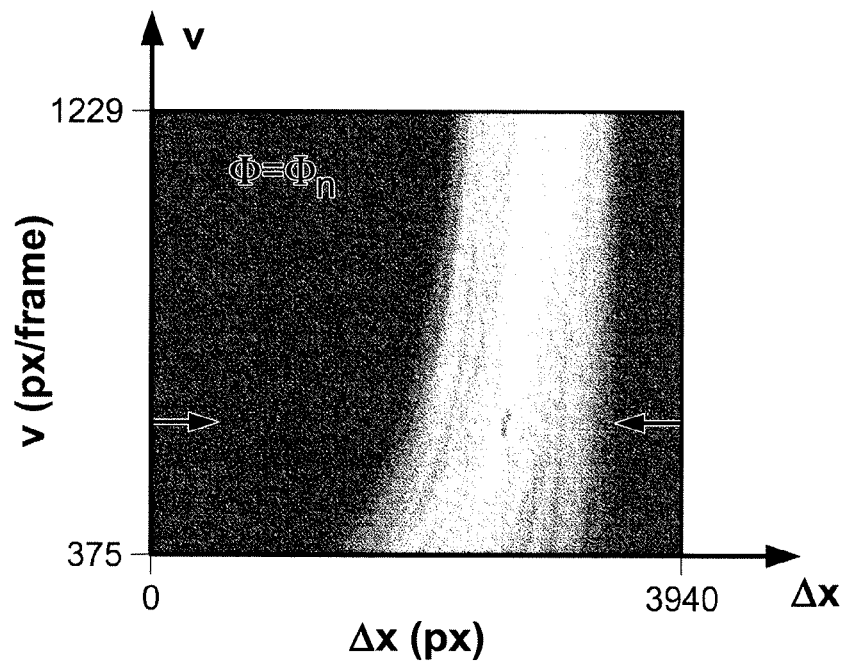
FIG. 2*g* is a single 2D slice highlight at the proper phase with arrows pointing to the velocity that matches the droplet velocity.
Figure 2H:
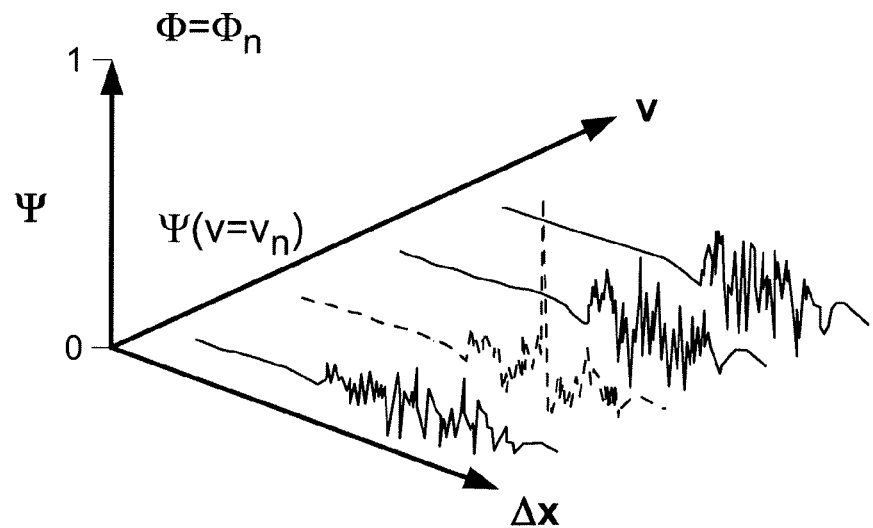
FIG. 2*h* is a graph of several cross sections at varying velocities demonstrating the sensitivity of the correlation function for the proper velocity.

In order to identify the "correct" correlation, a 3d matrix was first generated consisting of data that had correlation intensities for the all phases and velocities to be examined (FIG. 2f). In this case, five slices of separate phases are shown, and the correct phase of the droplet is highlighted in red. For each phase, the range of velocities that are appropriate were examined. To demonstrate the sensitivity to the velocity, a velocity scan from 375 px/frame to 1229 px/frame with 240 increments in between was shown. At a given velocity, a sharp peak in the heatmap on the 2D slice is observed, demonstrating that at the chosen phase, the droplet velocity matches a velocity of 493 px/frame. In reality, the number of velocities and phases that were scanned through were at a smaller range to improve computational efficiency.

Characterizing the Effect of Design Parameter Choices on Performance

To aid in the design and characterization of the device, several simulations were performed in MATLAB. The two questions investigated were: (i) how many bits in a pattern can be used to separate the signal from the background at a level where the Signal to Noise Ratio (SNR)=1 and (ii) how close can overlapping droplets exist before the peak from the correlation begins to overlap with the neighboring fluorescent droplet, making droplets undistinguishable. Noise was defined as Gaussian white noise that was added to the system.

Figure 3A:
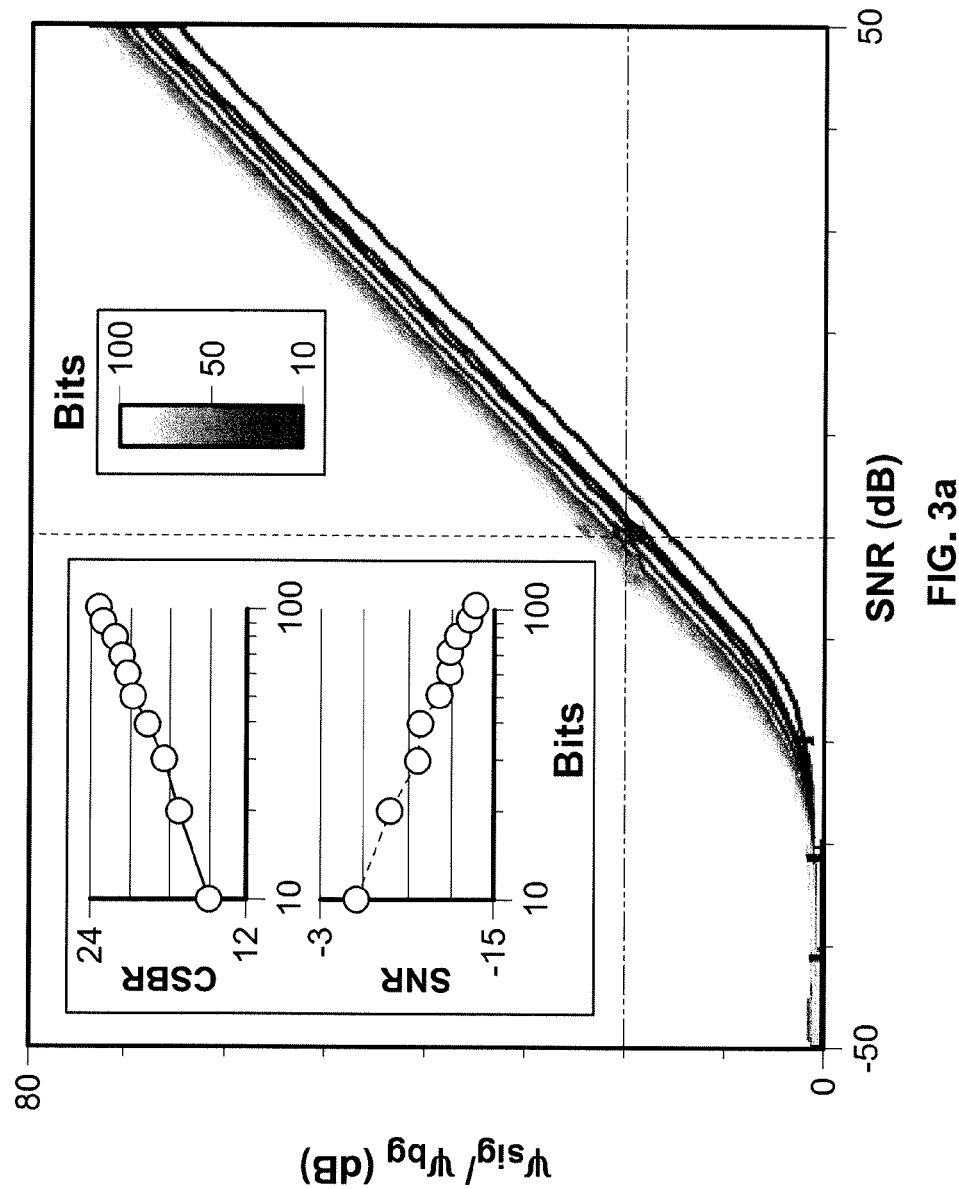
FIG. 3*a* is a graph showing the ratio of the correlation with a channel containing a signal to one without a signal and the signal to noise ratio as a function of the number of bits according to an embodiment of the present invention.

In order to simulate the first question, mask patterns of various MLS were generated with different number of "bits" corresponding to the length of the MLS. The length of the MLS ranged from 10 bits to 100 bits. Each MLS was given a width of 10 pixels to model the experimental setup, thus a 50 bit MLS was 500 pixels long. The correlation of a vector with ($\psi$sig) and without ($\psi$bg) a signal was compared at various noise levels the number of bits were scanned through. The root mean square (RMS) of the resulting correlation vectors around their peaks was taken, and this ratio was defined as the correlation signal to background ratio (CSBR=$\psi$sig/$\psi$bg). FIG. 3a shows the resulting CSBR as a function of both the number of bits and the SNR. Taking a vertical cut line at an SNR of 0 dB demonstrates how the CSBR increased as the number of bits was increased (FIG. 3a—Top inset). Taking a horizontal cutline shows that as we increase the number of bits, we can reach lower levels of resolvable SNR. This simulation showing that even when the SNR=0 dB, we are still able to resolve the CSBR 20 dB, demonstrating the power of using correlation for faint signals where noise may lead to false positives or false negatives otherwise.

Figure 3B:
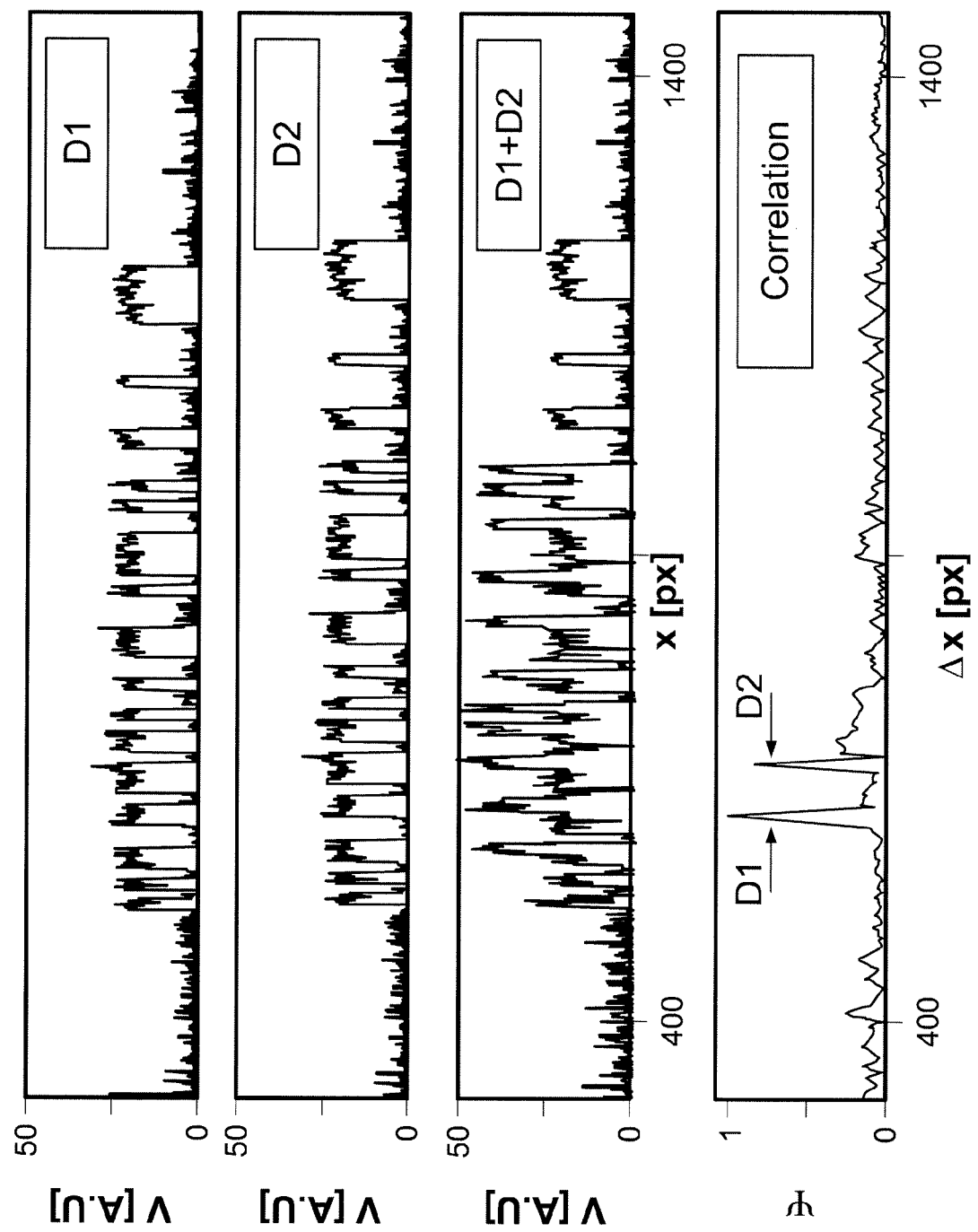
FIG. 3*b* shows a simulation of two separate signals which were added together and run through a correlation algorithm according to an embodiment of the present invention.

Based on this simulation and physical constraints set by the number of pixels in a given frame, 63 bits was selected for the MLS. While recording in 1920×1080p, this corresponds to the droplet taking up to 630 px/1920 px, or ⅓ of the frame. To find out how closely packed two droplets can be, two separate droplets were simulated, and their resulting signals added to create a sum consisting of the first and second droplet (FIG. 3b). The resulting correlation showed two sharply defined peaks that were 45 pixels apart (FIG. 3b), and moving these droplets closer would result in these peaks beginning to overlap.

Figure 3C:
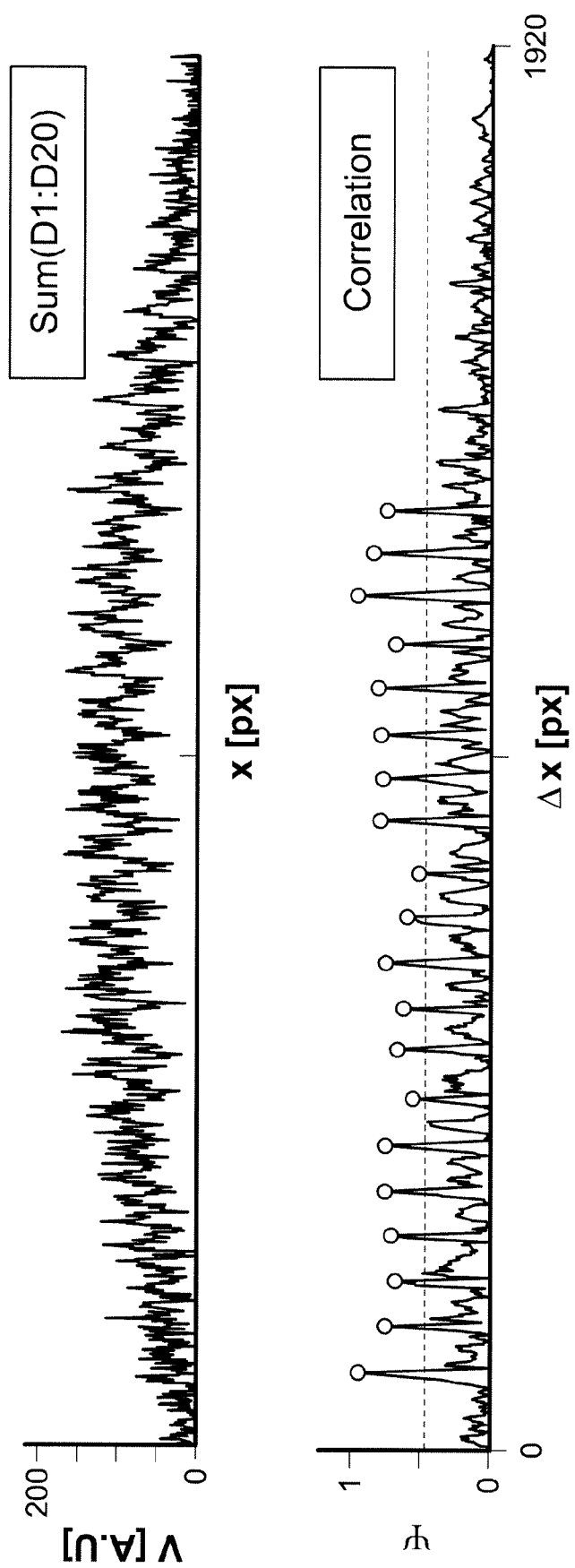
FIG. 3*c* shows a simulation of the signal of 20 droplets in a single channel and the resulting correlation according to an embodiment of the present invention.

How many droplets that could be packed in a given frame was then simulated, assuming they would be spaced in a sequential manner but their entry into the channel would be random to a degree where the droplets were not exactly evenly spaced. Each of the individual droplets when combined would create a signal that would be below the 256 RGB limit on the cell phone, and the resulting sum of the 20 droplets shows how the resulting signal looks impossible to identify the twenty patterns (FIG. 3c). By taking the correlation with the expected pattern, it was shown that the resulting correlation can recover the 20 separate droplets amidst this chaos.

Experimental Validation:

In order to validate the system, several features were highlighted that demonstrated the μMD's capability to identify droplets across a wide range of velocities, phase shifts, dynamic range, and fluorophore concentration.

Figure 4A:
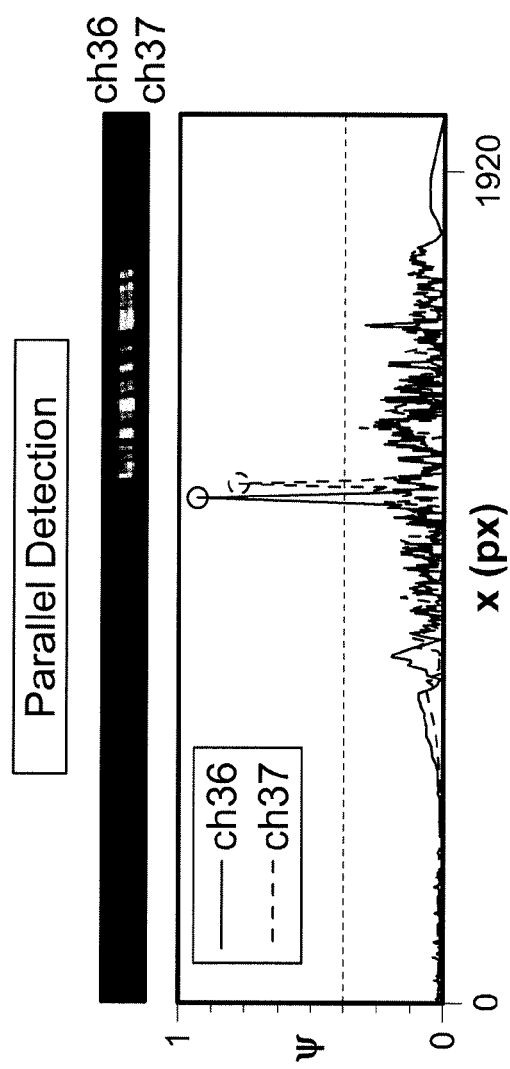
FIG. 4*a* shows experimental data of adjacent channels according to an embodiment of the present invention.
Figure 4B:
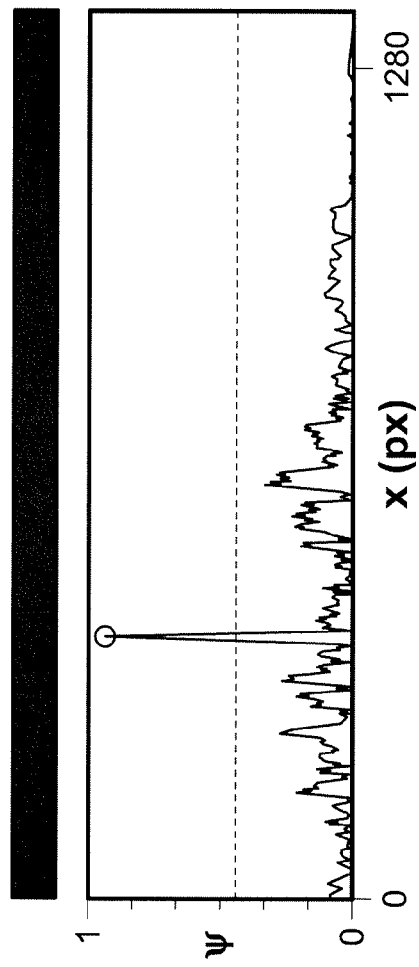
FIG. 4*b* shows the resolution of a barely visible droplet passing through a noisy background according to an embodiment of the present invention.
Figure 4C:
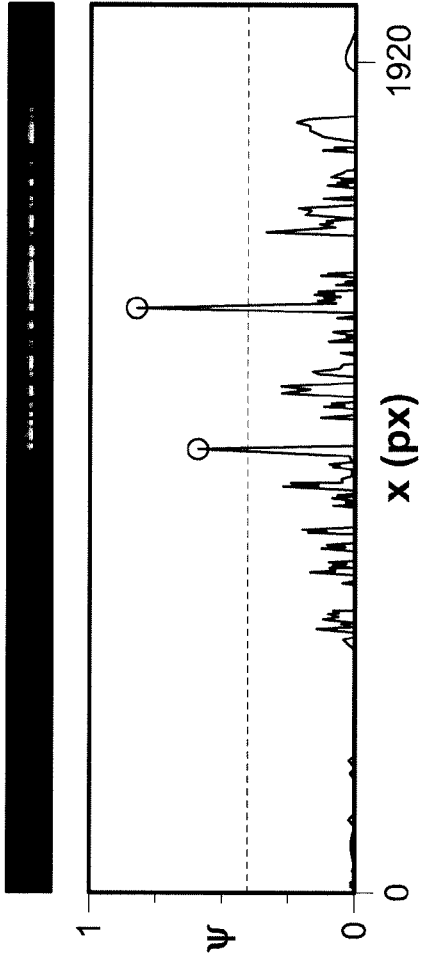
FIG. 4*c* shows the ability to resolve overlapping droplets using an MLS modulated sequence according to an embodiment of the present invention.

It was first shown that neighboring channels could be partitioned effectively into two separate segments based on the physical mapping of the camera. The fluorescent signal from a given channel did not leech into neighboring channels and affect the resulting correlation in nearby channels (FIG. 4a). To demonstrate that signals can be resolved even when they are comparable to the noise, a droplet with 500 nM fluorescent material was shown passing through the channel whose streak pattern is barely resolvable. However, when taking the correlation, a sharp peak separated from the background was seen allowing us to extract dilute concentrations of dye with comparable sensitivities to other droplet detector devices (FIG. 4b). Correlation not only resolved low signal droplets but also allowed separation of droplets that were overlapping. FIG. 4c shows two droplets where the pattern overlapped, but after running the algorithm two peaks were defined for each of the separate droplets.

Figure 4D:
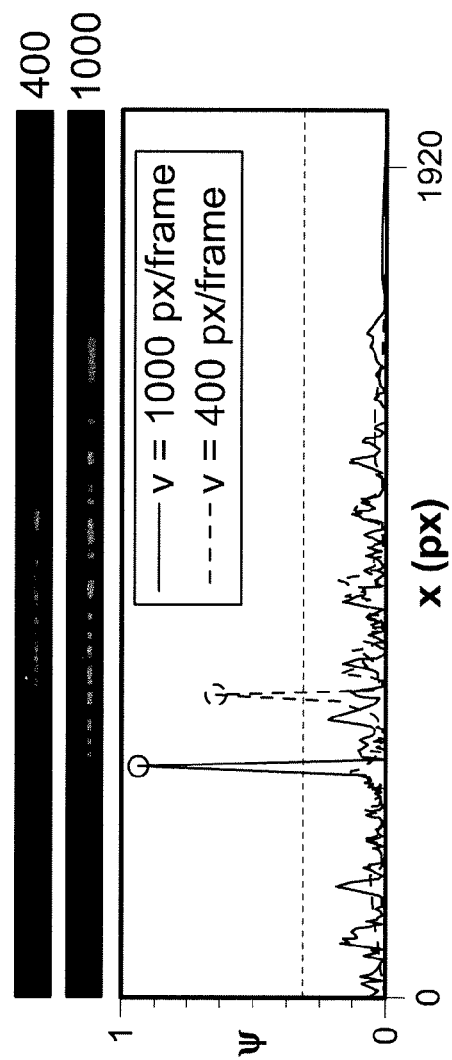
FIG. 4*d* shows the resolution of two droplets traveling at different flow rates according to an embodiment of the present invention.

To demonstrate the ability to scan through a wide range of velocities, two separate droplet signals were shown from two separate flow rates (FIG. 4d), one with a velocity of 400 px/frame and another with a velocity of 1000 px/frame. After scanning a set of velocities from 366 px/frame to 1229 px/frame which are chosen arbitrarily based on the data set, the ability to identify droplets even with a wide range of velocities was demonstrated. In reality, the velocity distribution of droplets was constrained so the scan for velocities was limited to a narrower range (for example, if droplets are designed to cover ⅓ of the frame, velocities from 500 to 700 px/frame can be scanned).

Figure 4E:
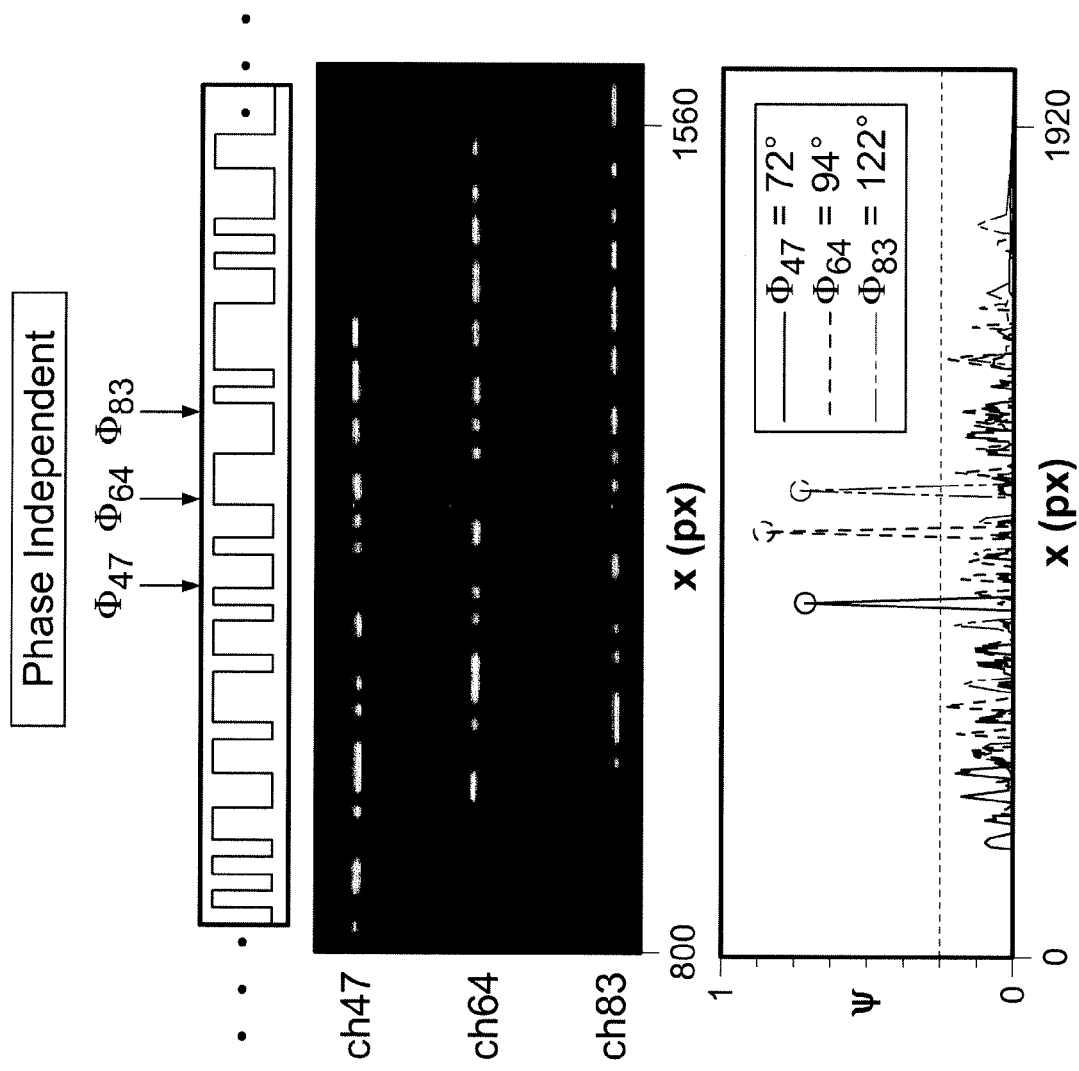
FIG. 4*e* shows an image and results showing the phase independent recovery of droplets despite the rolling shutter effect according to an embodiment of the present invention.

As mentioned, the rolling shutter effect and the mismatch of the LED MLS cycle with the frame rate capture of the cell phone caused an offset in the phase of the pattern. FIG. 4e shows three separate channels with different initial phases due to these effects. The initial phase for each droplet is highlighted above according to the user generated MLS uploaded to the Arduino. After scanning through phase for each of these patterns, it was possible to properly identify each droplet despite phase offsets.

Quantification of Device Sensitivity and Dynamic Range

In order to quantify the sensitivity of the device, a serial dilution was performed with dye to achieve a limit of detection down to 1 µM—a concentration limit below which biological assays are performed. 40 µm droplets were generated containing Dextran Rhodamine B 10,000 MW with 0.15 M MgSO4 (Thermo, D1824) for the dispersed phase and a continuous phase consisting of 0.65 cst Silicone Oil (Consolidated Chemical) with 5% v/v Span80. The dye was diluted at various concentrations and the signal to background ratio was measured using two methods. 1) First, the SBR was measured with the raw image only in the "R channel" of the RGB matrix, where the ratio of the droplet signal to the signal from an empty channel was taken and this was called the raw signal to background ratio (RSBR). 2) The background was then subtracted and the algorithm run. The correlation of a channel with a droplet and a channel without a droplet was taken, and the energy around the peak of the droplet was taken and divided by the energy of the background. This was called the correlation signal to background ratio (CSBR).

Figure 5A:
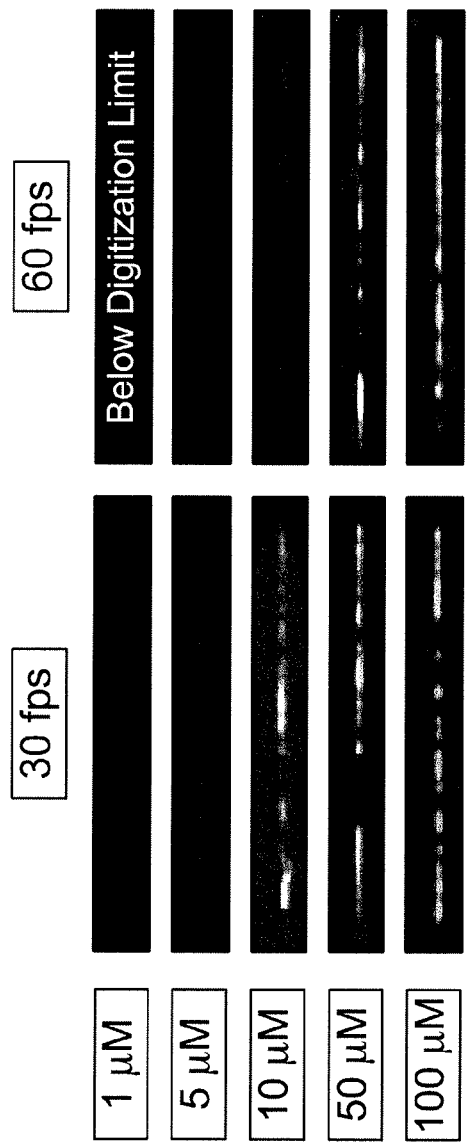
FIG. 5*a* shows raw images from a cell phone camera at two different frame rates according to an embodiment of the present invention.
Figure 5B:
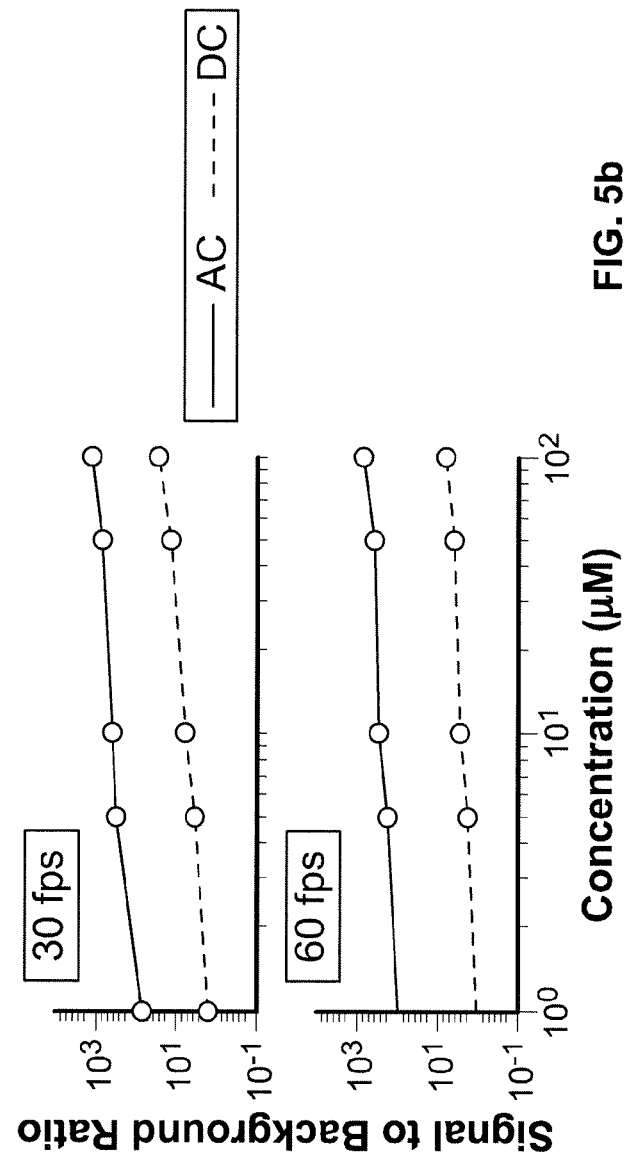
FIG. 5*b* shows a comparison of the DC SBR and AC correlation at the frame rates of 30 and 60 fps to demonstrate the ability to resolve low concentrations of fluorescent dye according to an embodiment of the present invention.

Raw images of the droplets at various concentrations and frame rates are shown (FIG. 5a), along with the RSBR and CSBR are plotted (FIG. 5b). Lower frame rates had a higher exposure time, allowing lower concentrations of dye to be detectable. Both followed a linear fit as expected, but as lower concentrations of dye were reached, the RSBR began to reach a ratio of 1 and was inseparable from the background. However, the CSBR was able to recover these low signal droplets and separate them from noise since the background noise did not contribute to any peaks in the background correlation vector. Using correlation, it was possible to resolve concentrations down to 1 µM that were overwhelmed by noise in the raw DC regime. While the RSBR flat lined to a ratio of 1, the reason we could not reach even lower concentrations of dye with correlation were due to the digitization effect of the CMOS camera. Since the RGB values only range from 0-256, we began to hit the digitization limit before lower concentration of dyes could be resolved (FIG. 5a).

Quantification of Dynamic Range

In order to quantify the dynamic range of the device, the capabilities were tested by spiking in a known number of fluorescent droplets into a known number of empty droplets. The droplets were then pipetted slowly to mix the sample to distribute the fluorescent droplets evenly among the empty droplets. Due to the ultra-high throughput detection speed, it was possible to sample large volumes of droplets to reach sensitivities that cannot be afforded by typical systems. Since most digital assays use ~µL scale volumes, they are often limited to the maximum sensitivity of rare targets. For example, Biorad's 20,000 droplets of 20 µL of sample allow for a detection of 50 targets in 1 mL, if 1:20,000 droplets are positive leading to high variability. Here, it was shown that with the ability to process large samples rapidly it was possible to image droplets as low as 1 in $10^7$<5 minutes to enable detection of extremely rare genes in a large background population (KRAS gene in pancreatic cancer), or sparse sample in a large volume (HIV monitoring for patients on treatment).

The dynamic range tested ranged from 3 fluorescent droplets to $10^6$ fluorescent droplets in 1 mL of oil (this was tested in ~$3*10^7$ empty droplets, which is equal to 1 mL of sample). The empty droplets correspond to 1 mL of empty sample that were converted into 40 µm diameter droplets. Both sets of droplets were made on flow-focusing devices to create a narrow CV for the droplet diameters to account for any variation from droplet volume size. In order to make the titrations, 1 mL of fluorescent dye were used to create ~$3*10^7$ droplets, and a known volume based of this starting amount was spiked into each of the syringes that were run. Due to variations in the spiked sample vs observed due to droplet sedimentation, droplet concentrations were verified by measuring the percent of positive droplets on a fluorescent microscope (Leica) as well as visually counting the droplets in the video for the low concentrations.

In order to count droplets as they moved through the frame, the resulting correlation vectors were used for each of the channels to calculate the number of true droplets (FIG. 5c). Since a droplet could potentially peak two or three times based on its entry into the channel, repeat peaks were removed based on the reoccurrence of the correlation max if it repeated in an expected location in the next one or two frames.

Figure 5E:
FIG. 5*e* shows droplets at various concentrations travelling through the frame according to an embodiment of the present invention.
Figure 5E:
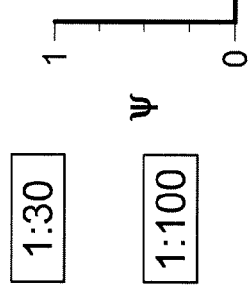
Figure 5F:
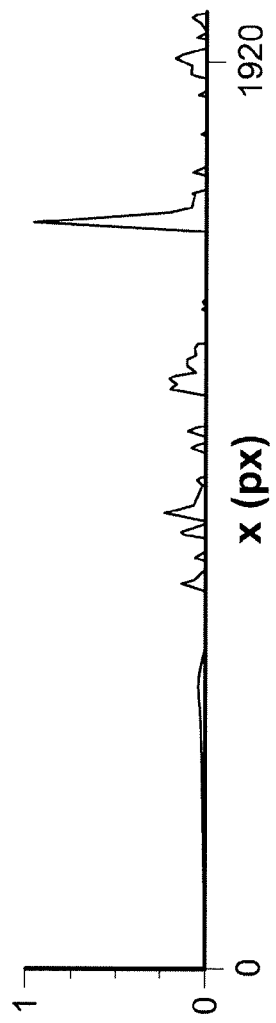
FIG. 5*f* shows the resolution of the droplets appearing in the image of FIG. 5*e*.

The requirement to have at least two correlation peaks in successive frames based on the droplet's velocity also removed any erroneous peaks that may exist from noise, and thus the system was both robust to peaks from background and did not over count droplets. A linear fit was shown between the number of the spiked number of fluorescent droplets and the measured ones for each set (FIG. 5d). FIG. 5e shows raw images of several channels at different concentrations, while showing the ability to resolve highly overlapping droplets despite the frame looking overcrowded with overlapping patterns (FIG. 5f). The data followed a linear fit as expected, and variations from the linear fit could be attributed to Poisson error.

It was demonstrated that due to the extremely parallelized detection scheme, 108 droplets could be observed in as little as three minutes, a 1000-fold reduction compared to the commercial systems. The upper limit of the dynamic range corresponded to when overlapping signals from fluorescent droplets became unresolvable. The lower limit could theoretically be further improved by running more samples, but 3 droplets/mL corresponds to extremely rare events that were believed to be sufficient for most digital assays.

DISCUSSION

Dynamic Range Vs Throughput:

It was shown that simulations and experimental data matched closely. Furthermore, the number of fluorescent droplets that fill a channel at this concentration corresponded to ~2% positive droplets in the channel at a given time. Dynamic range is defined as the ability to detect droplets that are positive with fluorescent dye, whereas throughput is defined as the total volume that can be processed through the device based on the flow rate. Positive droplets signify the number of droplets containing a biological target since in digital assays, positive droplets fluoresce larger. In many digital assays, most targets are in rare abundance, which is the reason digital assays are so powerful in increasing the concentration of the target within a confined volume.

For throughput, it was found that when a cream of droplets alone with minimal oil spacing was passed that the droplets would often cluster around the channel inlet and outlet and could clog the channel entrance. This clogging prevents the velocity distribution spread to be even, so spacing oil was added between the droplets. Spacing oil is often a result of droplet generation where the oil flow rate is larger than the aqueous flow rate, creating naturally gaps. While work has been done to eliminate spacing oil, it was found that spacing oil could help allow droplets to travel through without clogging the channels. When the droplet fraction compared to the total volume was <50%, minimal clogging and variations on the velocity distribution were observed. While negative droplets can be useful to count in the total droplets detected per sample, since most the droplets are empty and droplet formation creates droplets that are monodisperse, the total droplets that have passed can be approximated by the known droplet diameter. For example, if 1 mL of sample is run, the number of droplets based on their diameter are [35 µm, $4.45*10^7$], [40 µm, $3*10^7$], or [45 µm, $2*10^7$]. Thus, for rare detection where the targets are less than $10^5$ copies/mL, the variation from this assumption of fraction of fluorescent droplets are [0.225%, 0.3351%, 0.447%], respectively.

Effect of droplet diameter and pattern: Droplets that are much larger than 40 µm tended to squish through the channels of imaging. As these droplets squeeze through, they tended to change shape into ovals that spread out, and the time modulation began to see a smoothing effect based on this oval shape. Rather than seeing droplets as a point, the emission began to overlap with regions that should have been "off" and affected the pattern. Droplets that were much smaller than the 40 µm width of the channel did act as points, but since the intensity scales in a cubic manner with the droplet diameter, droplets that are really small tend to emit too little light to be detected by the cell phone.

Tradeoff between design parameters: There were several constrains we previously described for selecting design considerations such as droplet streak length, number of bits etc. However, there are several other variables designed based on the scenario. One selection was the frame rate of the cell phone camera and the limit of detection effect. As the frame rate of the camera was increased, it was possible to increase the throughput since more droplets could be analyzed. However, as the frame rate was increased, there was less exposure for the CMOS, so the limit of detection decreased. Therefore, a lower fps was used for detecting sensitive assays.

Next, as the flow rate increased, the streaks became larger and the total intensity of the droplet spread over the streak length. If the flow rate was too slow, the streaks became shorter and it was difficult to resolve the patterns, while if the total streak exceeded 1920 px, the entire pattern did not fit on the frame. Therefore, for each frame rate, the flow rate was selected such that each droplet took about ⅓ of the screen—both for counting the droplets as they moved frame by frame and so that their lengths were large enough to contain enough bits for the patterning.

In addition, there are several camera settings that could be changed to alter the video acquisition. High ISO for bright droplets can lead to saturation too early making overlapping droplets harder to resolve since the pattern becomes saturated. For most biological assays, this should not be an issue since it is unusual to measure droplets with concentrations of 100 µM or more.

A cloud based server could also be used for calculations. In the examples above, data was taken off the smartphone and processed in Matlab on a desktop computer. By beaming the data to a server for processing, the user could directly receive the droplet counts on their smartphone. While parallel computing in Matlab was efficient with the parallel computing toolbox, the processing may be further optimized by switching to a vectorized program that can process the correlation computations needed faster.

We claim:
1. A device comprising:
   a light source configured to illuminate a plurality of droplets passing through a microfluidic channel;
   a controller configured to flash the light source in a time-domain modulated sequence; and
   a photo sensor configured to capture an image of the microfluidic channel,
   wherein the time-domain modulated sequence has a duration, d, wherein the image has an exposure time, t, and wherein t is greater than or equal to d.
2. The device of claim 1, wherein the light source is a light-emitting diode (LED).
3. The device of claim 1, wherein the photo sensor is a complementary metal-oxide-semiconductor (CMOS) photo sensor.
4. The device of claim 3, wherein the CMOS photo sensor is part of a DSLR camera, a point-and-shoot camera, a cellular phone camera, or a medium format camera.
5. The device of claim 3, wherein the CMOS photo sensor is at least 1/3.2" diagonal.
6. The device of claim 1, wherein the time-domain modulated sequence is a pseudorandom sequence.
7. The device of claim 1, wherein the time-domain modulated sequence is a minimally correlating maximum length sequence.
8. The device of claim 7, wherein the maximum length sequence is ⅟30 sec or less.
9. The device of claim 8, wherein the maximum length sequence is ⅟60 sec or less.
10. The device of claim 1, wherein the photo sensor is configured to capture a video of the microfluidic channel.
11. The device of claim 10, wherein the video has a frame rate of at least 30 fps.

* * * * *

UNITED STATES PATENT AND TRADEMARK OFFICE
CERTIFICATE OF CORRECTION

| | | |
|---|---|---|
| PATENT NO. | : 11,630,052 B2 | Page 1 of 1 |
| APPLICATION NO. | : 17/017966 | |
| DATED | : April 18, 2023 | |
| INVENTOR(S) | : David A. Issadore et al. | |

It is certified that error appears in the above-identified patent and that said Letters Patent is hereby corrected as shown below:

In the Specification

<u>Column 1</u>,
Before the Heading FIELD OF THE INVENTION at Line 17, insert the following Heading and Paragraph:
-- GOVERNMENT RIGHTS
This invention was made with government support under W81XWH-19-2-0002 awarded by the Medical Research and Development Command. The government has certain rights in the invention. --.

Signed and Sealed this
Fifth Day of December, 2023

Katherine Kelly Vidal
*Director of the United States Patent and Trademark Office*